US006918887B1

(12) United States Patent
Gremel et al.

(10) Patent No.: US 6,918,887 B1
(45) Date of Patent: *Jul. 19, 2005

(54) VENOUS FILTER FOR ASSISTED VENOUS RETURN

(75) Inventors: Robert F. Gremel, Huntington Beach, CA (US); Roger J. Elgas, Anaheim Hills, CA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/324,176

(22) Filed: Dec. 19, 2002

Related U.S. Application Data

(63) Continuation of application No. 09/954,787, filed on Sep. 18, 2001, now Pat. No. 6,524,267, which is a continuation of application No. 09/251,619, filed on Feb. 17, 1999, now Pat. No. 6,302,860.

(51) Int. Cl.[7] ............................................. A61M 37/00
(52) U.S. Cl. .................. 604/6.09; 604/6.11; 604/6.15; 604/319; 210/120
(58) Field of Search ............................. 604/4.01, 5.01, 604/5.02, 5.03, 5.04, 6.01, 6.02, 6.03, 6.04, 604/6.05, 6.06, 6.07, 6.08, 6.09, 6.1, 6.11, 604/6.12, 6.13, 6.14, 6.15, 6.16, 7, 65, 67, 604/73, 122, 405, 406, 129, 317–319, 403, 604/404, 123, 128; 210/436, 739, 741, 744, 210/749, 805, 90, 120, 188, 472, 539; 422/44, 422/45, 47, 48; D24/162; 417/1; 261/DIG. 28; 95/241, 243

(56) References Cited

U.S. PATENT DOCUMENTS

| | | |
|---|---|---|
| 3,507,395 A | 4/1970 | Bentley ....................... 210/443 |
| 4,205,677 A | 6/1980 | Engstrom |
| 4,402,687 A | 9/1983 | Denty et al. |
| 4,411,783 A | 10/1983 | Dickens et al. ............. 210/304 |
| 4,490,331 A | 12/1984 | Steg, Jr. ....................... 422/46 |
| 4,572,724 A | 2/1986 | Rosenberg et al. ........... 55/159 |
| 4,573,992 A | 3/1986 | Marx |

(Continued)

FOREIGN PATENT DOCUMENTS

| | | |
|---|---|---|
| DE | 4326886 A1 | 2/1995 |
| EP | 0351980 B1 | 4/1994 |
| EP | 1036567 A2 | 9/2000 |
| WO | WO 96/24397 | 8/1996 |
| WO | WO 00/12155 | 3/2000 |

OTHER PUBLICATIONS

*Journal of Extra-Corporeal Technology*: "Rapid Pediatric Cardiopulmonary Support System," J.W. Ojito, et al., 1997; 29(2):96–99.

(Continued)

*Primary Examiner*—Nicholas D. Lucchesi
*Assistant Examiner*—Jennifer J Maynard
(74) *Attorney, Agent, or Firm*—Michael Best & Friedrich LLP

(57) ABSTRACT

The need for a venous reservoir in a heart-lung machine is obviated by using a vacuum-purged negative-pressure air filter in the venous return line ahead of the main blood pump. The purging vacuum for the venous air filter can also be used to purge air from the cardiotomy reservoir if a backflow-preventing valve is used on the venous air filter.

26 Claims, 2 Drawing Sheets

U.S. PATENT DOCUMENTS

| | | | |
|---|---|---|---|
| 4,923,438 | A | 5/1990 | Vasconcellos et al. |
| 4,997,464 | A | 3/1991 | Kopf |
| 5,039,482 | A | 8/1991 | Panzani et al. |
| 5,049,146 | A | 9/1991 | Bringham et al. |
| 5,055,198 | A | 10/1991 | Shettigar .................... 210/650 |
| 5,061,236 | A | 10/1991 | Sutherland et al. |
| 5,074,839 | A | 12/1991 | Choksi et al. |
| 5,158,533 | A | 10/1992 | Strauss et al. ................. 604/4 |
| 5,162,102 | A | 11/1992 | Nogawa et al. ............... 422/48 |
| 5,205,153 | A | 4/1993 | Hlavinka et al. .......... 73/79.03 |
| 5,238,655 | A | 8/1993 | Laible et al. |
| 5,270,005 | A | 12/1993 | Raible ......................... 422/46 |
| 5,382,227 | A | 1/1995 | Riquier |
| 5,419,769 | A | 5/1995 | Devlin et al. |
| 5,573,526 | A | 11/1996 | Hess |
| 5,632,894 | A * | 5/1997 | White et al. ................. 210/436 |
| 5,823,986 | A | 10/1998 | Peterson |
| 5,876,611 | A * | 3/1999 | Shettigar .................... 210/739 |
| 5,931,646 | A | 8/1999 | Nogawa et al. |
| 6,017,493 | A | 1/2000 | Cambron et al. |
| 6,200,276 | B1 | 3/2001 | Biesel et al. |
| 6,302,860 | B1 * | 10/2001 | Gremel et al. ............. 604/6.09 |
| 6,337,049 | B1 * | 1/2002 | Tamari ........................ 422/44 |
| 6,524,267 | B1 * | 2/2003 | Gremel et al. ............. 604/6.09 |

OTHER PUBLICATIONS

*Pediatric Cardiac Anesthesia*: "Extracorporeal Circulation and Circulatory Assist Devices in the Pediatric Patient," Frank H. Kern, et al., 1997; 3rd Ed.:219-258.

*Journal of Extra-Corporeal Technology*: "Experimental Use of an Ultra-Low Prime Neonatal Cardiopulmonary Bypass Circuit Utilizing Vacuum-Assisted Venous Drainage," Edward Darling, et al., 1998; 30(4):184-89.

*Perfusion*: "Minimizing The Bypass Circuit: A Rational Step In The Development of Paediatric Perfusion," Martin Elliott, 1993; 8:81-86.

*Zasshi Journal* (English Anstract): "The Indications and Limitations of Open Heart Surgery Without Homologous Blood Transfusion in Children and Infants," Masanobu Maeda, et al., 1994; 42:1-7.

*Journal of Cardiovascular Surgery*: "Clear Prime for Infant Cardioplumonary Bypass: A Miniaturized Circuit," Eric Wabeke, et al., 1988; 29(2):117-22.

*Journal of Extra-Corporeal Technology*: "A Modification Of The Sarus Conducer Heat Exchanger As A Low Prime Pediatric Cardioplegia System," Ronald Gorney, et al., 1994; 26(1):37-39.

*International Anesthesiology Clinics*: "Pediatric Cardiopulmonary Bypass: A Review of Current Practice," Robert C. Groom, et al., 1996; 34:141-63.

*Journal of Extra-Corporeal Technology*: "Micro-Prime Circuit Facilitating Minimal Blood Use During Infant Perfusion," Charles M. Tyndal Jr., et al., 1987, 19(3):352-57.

*Ann. Thoracic Surgery*: "A Venous Reservoir For Cardiopulmonary Bypass In Newborns and Small Infants," John L. Ochsner, et al., 1988; 45:686.

*Proc. Eur. Society Artifical Internal Organs*: "Automation of Cardiopulmonary Bypass for Open Heart Surgery," P.H. Mook, et al., 1978; 5:234-37.

*Perfusion*: "Mini-Circuit Cardiopulmonary Bypass With Vacuum Assisted Venous Drainage: Feasibility Of An Asanguineous Prime IN the Neonate," Christine L. Lau, et al., 1999; 14:389-96.

*Artificial Organs*: "A Novel Technique for Cardiopulmonary Bypass Using Vacuum System for Venous Drainage with Pressure Relief Valve: An Experimental Study," Satoshi Taketani, et al., 1998; 22(4):337-41.

*Perfusion*: "Paediatric Perfusion Practice in North America: An Update," Robert C. Groom, et al., 1995; 10:393-401.

*Perfusion*: "Single Pump Mechanically Aspirated Venous Drainage (SPMAVD) for Cardiac Reoperation," 1996; 11: 351-353 (Applicants only have p. 351).

*Ann. Thoracic Surg*: "Minmally Invasive Coronary Artery Bypass Grafting," Tea E. Acuff, M.D., et al., 1996; 61:135 (Applicants only have p. 135).

*Ann. Thoracic Surg.*: "Transpericardial Inferior Vena Caval Cannulation in Thoracic Aorta Operations," Eugenio Neri, M.D., et al., 1996; 62:1208 (Applicants only have p. 1208).

*Ann. Thoracic Surg.*: "Minimally Invasive Valve Operation," Delos M. Cosgrove III, M.D., et al., 1998; 65:1535 (Applicants only have p. 1535).

*Ann. Thoracic Surg.*: "Augmented Femoral Venous Return," Lynn Solomon, M.D., et al., 1993; 55:1262 (Applicants only have p. 1262).

Drawing provided to Applicants by Miami Children's Hospital, no date shown.

Specification Sheets of a venous assisted CB cicruit, specification sheets sent between Miami Children's Hospital and Medtronic, Inc., earliest date is Dec. 16, 1998 (7 pages).

Specification Sheets of a hybrid CB circuit, specification sheets sent between Miami Children's Hospital and Medtronic, Inc., earliest date is Jun. 20, 1997.

Email relating to augmented venous return sent to PertList@aol.com, PerfList@aol.com is a multiple recipient medical informational email group, sent on Apr. 27, 1997.

Email relating to augmented venous return and minimally invasive procedures sent to PerfList@aol.com, PerfList@aol.com is a multiple recipient medical informational email group, sent on Apr. 27, 1997.

Email relating to venous drainage sent from Brian Crawford CCP to Jorge Ojito on Apr. 28, 1997.

Email relating to augmented venous return sent by Jorge Ojito on Apr. 26, 1997

*Ann. Thoracic Surgery*, "Assisted Venous Drainage Cardiopulmonary Bypass in Congential Heart Surgery," Jorge Ojito, et al., 2001; 71:1267-72.

Ann. Thoracic Surgery: "Rapid Cardiopulmonary Support for Children with Complex Congenital Heart Disease," Jeffrey P. Jacobs, et al., 2000;70:742-50.

"Minimally Invasive & Bypass" computer search results, 1998.

"Minimally Invasive & Valve" computer search results, 1998.

"Intersept® Tubing Pack with Carmeda® BioActive Surface" product label, 2003.

Facsimile transmission sheet form Elly Wierenga, Medtronic, Inc., regarding Carmeda® Data Analysis, Sep. 14, 1998.

"Venous Pull Circuit" diagram.

*Journal of Thoracic and Cardiovascular Surgery* Copyright and Conflict of Interest Statement regarding manuscript entitled "Assisted Venous Drainage Cardiopulmonary Bypass: (AVDCPB) An Alternative Technique in Minumally Invasive Congenital Surgery" signature page, signed by Jorge Ojito, Nov. 25, 1998.

May 4, 1999 correspondence from John A. Waldhausen, M.D., *The Journal of Thoracic and Cardiovascular Surgery*, to Redmond Burke, M.D. regarding his manuscript entitled "Assisted Venous Drainage Cardiopulmonary Bypass: an Alternative Technique in Minimally Invasive Congenital Cardiac Surgery."

Jun. 28, 2000, Correspondence from L. Henry Edmunds, Jr., M.D., Editor, *The Annals of Thoracic Surgery*, to Redmond P. Burke, M.D. regarding his paper entitled "Assisted Venous Drainage Cardiopulmonary Bypass: Safety and Efficacy in Congential Heart Surgery."

*Curriculum Vitae* of Jorge Ojito.

Declaration of Yehuda Tamari in the matter of United States patent No. 6,302,860 and 6,524,267.

*Curriculum vitae* of Yehuda Tamari.

Program and certificate of participation of Jorge Ojito at Sociedad Chilenade Circulacion Extracorporea, Vina del Mar, Chile, Nov. 12-15, 1998.

"Assisted Venous Drainage Cardiopulmonary Bypass: Safety and Efficacy in Congenital Heart Surgery" presentation, Jorge Ojito.

Certificates of participation by Jorge Ojito Jornados Sobre Perfusion Pediatrica y Asistencia Circulatoria Mecaanica, Buenos Aires, Argentina, Nov. 17, 1998.

Cardiologic program, Caracas, Venezuela, Jun. 6-10, 2000.

"Assisted Venous Drainage Cardiopulmonary: Safety and Efficacy in Congenital Heart Surgery," presented by Jorge Ojito, Mechansims of Perfusion XVI, Lake Buena Vista, Florida, May 17-20, 2001.

"Assisted Venous Drainage During CPB: Safety and Efficacy in Congenital Heart Surgery ," presented by Jorge Ojito, The 38th Annual Scientific Meeting of Japanese Society of Pediatric Cariology and Cardiac Surgery, 2002.

File history of United States patent No. 6,302,860 (Gremel, et al.).

Comparison of claims in United States Patent No. 6,302,860 (Gremel, et al) and United States patent No. 6,337,049 (Tamari).

Declaration of Jorge Ojito in the matter of United States patent No. 6,302,860 and 6,524,267, Aug. 2003.

\* cited by examiner

VENOUS FILTER FOR ASSISTED VENOUS RETURN

This application is a continuation under 35 U.S.C. 120 of U.S. application Ser. No. 09/954,787, filed on Sep. 18, 2001, Now U.S. Pat. No. 6,524,267, which in turn is a continuation of U.S. application Ser. No. 09/251,619, filed on Feb. 17, 1999, and now U.S. Pat. No. 6,302,860.

FIELD OF THE INVENTION

This invention relates to blood filters used in cardiopulmonary bypass circuits, and more particularly to a negative pressure blood filter for use in the venous line whether using assisted venous return techniques or not.

BACKGROUND OF THE INVENTION

Conventional cardiopulmonary bypass uses an extracorporeal blood circuit which includes a venous drainage line, venous reservoir, blood pump, oxygenator, and arterial filter. Blood circulation is accomplished by draining blood from the patient by gravity through the venous drainage line to the venous reservoir. From there, blood drains down to the blood pump, placing this portion of the circuit at a negative pressure with respect to atmosphere. The pump supplies positive pressure to return the blood to the patient through the oxygenator and filter. The venous reservoir holds blood volume as required, while both the venous reservoir and arterial filter remove air bubbles from the blood. These may cause health problems if returned to the patient in the arterial blood flow. Air can enter the circuit from a number of sources, including around the venous cannula and through various unanticipated intra-operative events. A further complication arises if a centrifugal pump is used, in which case a large volume of air will de-prime the pump, depriving it of its pumping capability.

In order to remove air from an extracorporeal circuit prior to its use, the circuit is primed with an appropriate solution. During surgery, this solution dilutes the patient's blood, and it is therefore desirable to minimize the volume required. The venous reservoir contains a relatively large volume of fluid, and recently it has been proposed to eliminate this component of the circuit. Several problems arise, however. Without the venous reservoir between the patient and the oxygenator, any air in the venous line will either accumulate in the centrifugal pump (if used) or be pumped into the oxygenator. Furthermore, if a large bolus of air is introduced, it may de-prime the pump and oxygenator. Although arterial filters are designed to capture air bubbles, they are not designed to handle larger volumes of air such as may occur from the causes described above. Also, arterial filters are located downstream of both the pump and the oxygenator, and therefore cannot prevent air problems that would occur in those devices. Furthermore, conventional arterial filters are designed to operate at positive blood pressures.

SUMMARY OF THE INVENTION

The present invention improves upon the design of an arterial filter to allow it to be used as a venous filter at a negative pressure and to capture larger volumes of air.

DESCRIPTION OF THE PREFERRED EMBODIMENT

Figure 1:
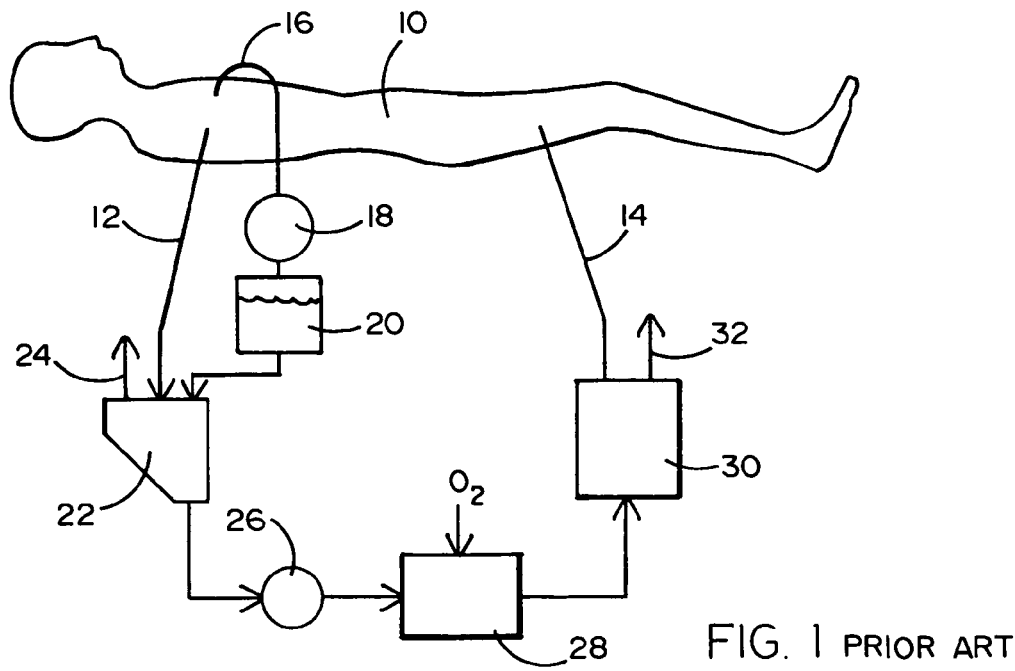
FIG. 1 is a schematic diagram of a conventional heart-lung machine.

Conventional heart-lung equipment, as schematically depicted in FIG. 1, draws the blood of a patient 10 during cardiovascular surgery through a venous line 12, oxygenates it, and returns the oxygenated blood to the patient 10 through an arterial line 14. Cardiotomy blood and surgical field debris are aspirated by a suction device 16 and are pumped by pump 18 into a cardiotomy filter 20.

In a conventional extracorporeal blood circuit, venous blood from line 12, as well as defoamed and filtered cardiotomy blood from filter 20, are discharged into a venous reservoir 22. In the reservoir 22, air entrapped in the venous blood (as, for example, air drawn into the blood circuit through the sutures, not shown, that attach the venous line 12 to a vein of the patient 10) rises to the surface of the blood in the reservoir 22 and is vented to atmosphere through a purge line 24. The purge line 24 is typically about a 6 mm ID line, and the air space above the blood in reservoir 22 is substantial.

In the conventional circuit of FIG. 1, a pump 26 draws blood from the reservoir 22 and pumps it through an oxygenator 28 and an arterial filter 30 into the arterial line 14. The arterial filter is basically a bubble trap that traps any microair bubbles larger than about 20–40 $\mu$m and discharges them to atmosphere through a typically about 1.5 mm ID purge line 32.

Figure 2:
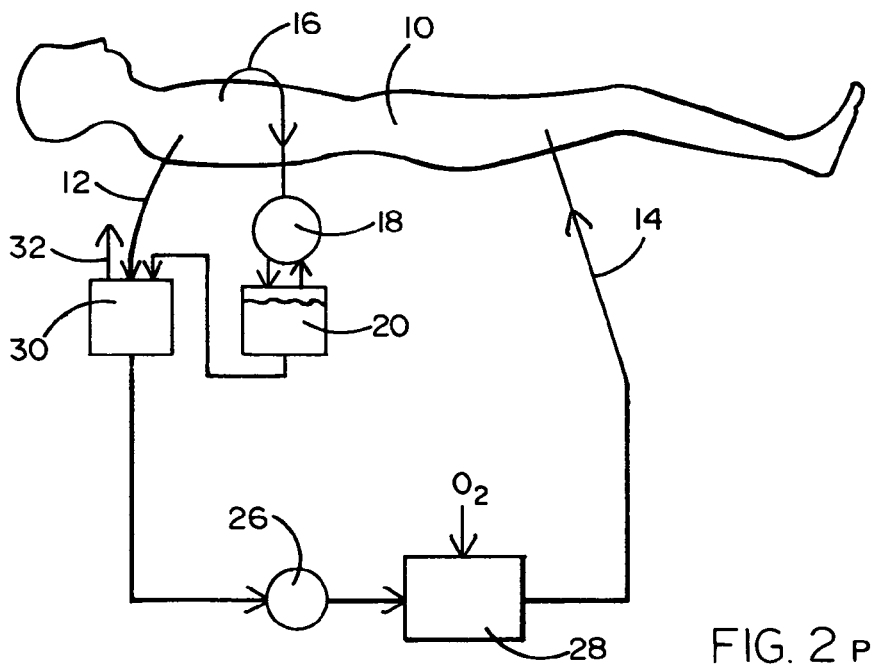
FIG. 2 is a schematic diagram of an AVR type heart-lung machine.

As shown in FIG. 2, it has recently been proposed to produce an assisted venous return (AVR) and to eliminate the reservoir 22, which accounts for a major portion of the priming volume of the extracorporeal blood circuit, by moving the arterial filter 30 into the venous line 12, upstream of the pump 26.

The filter 30 does not have an air space between its inlet and outlet, as the venous reservoir 22 does. Consequently, the negative pressure caused on the outlet side of filter 30 in FIG. 2 by the pump 26 is transmitted as suction to the venous line 12, thereby assisting the venous return from the patient 10.

Figure 3:
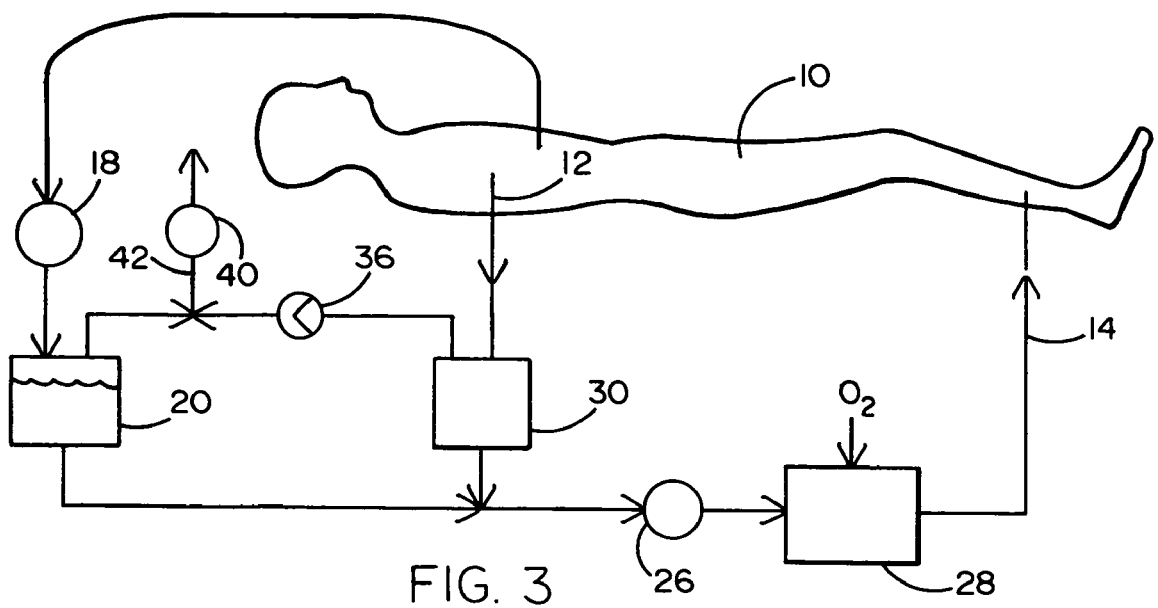
FIG. 3 is a schematic diagram of a heart-lung machine in accordance with the invention.

In accordance with the invention (FIGS. 3 and 4), a filter 30 of the type and size conventionally used as an arterial filter is adapted for efficient use as an AVR filter by several modifications. First, evacuation of air is facilitated by increasing the size of the purge port 34 to accept, e.g., a 6 mm ID purge line. Secondly, a vacuum greater than that normally used for venous drainage is applied to the purge port 34 to actively purge air from the filter 30. Thirdly, a check valve 36 is incorporated into the purge port to prevent air or blood from the cardiotomy reservoir 20 (which is at ambient pressure but is conveniently purged by the same vacuum that purges filter 30) from being drawn into the filter 30 by the negative pressure in filter 30, when the purging vacuum is not active. Fourthly, an air sensor 38 is provided in the filter 30 and is connected to activate the purge vacuum when, and only when, air is present in the filter 30. This prevents blood from being aspirated by the purging vacuum.

The purging vacuum may be produced by a pump 40, or it may be produced by connecting the purge line 42 to the vacuum outlet conventionally provided in operating rooms.

Figure 4:
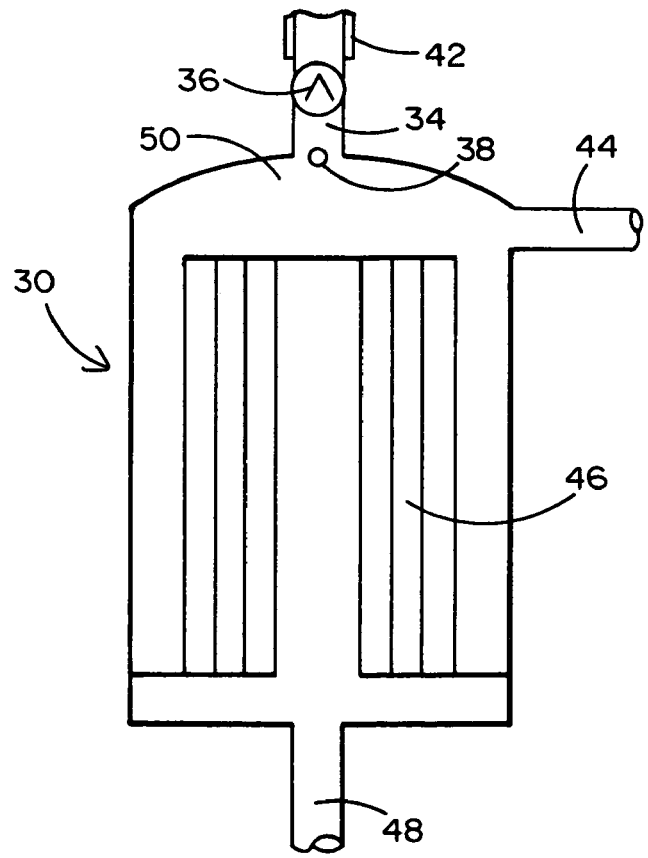
FIG. 4 is a partly schematic vertical section of the inventive filter.

FIG. 4 shows in somewhat schematic form the filter 30 of this invention. Blood enters the filter 30 through an inlet 44 and is drawn through the filter element 46 and into the outlet 48 by the action of pump 26. A screen (not shown) or other conventional bubble-trapping device traps any air bubbles in the blood stream and causes them to rise to the top 50 of filter 30. Normally, the filter 30 is filled with blood. When air begins to accumulate at the top of filter 30, this fact is sensed by the air sensor 38. The sensor 38 activates the vacuum in the purge line 22. The vacuum at the purge port 34 overcomes the negative pressure in the filter 30 and draws out any accumulated air, shutting off under the control of sensor 38 when all the air has been removed.

It is understood that the exemplary venous filter for assisted venous return described herein and shown in the drawings represents only a presently preferred embodiment of the invention.

Indeed, various modifications and additions may be made to such embodiment without departing from the spirit and scope of the invention. Thus, other modifications and additions may be obvious to those skilled in the art and may be implemented to adapt the present invention for use in a variety of different applications.

What is claimed is:

1. A device for removing air from venous blood of a patient, comprising:
    a container having a blood inlet for receiving the venous blood, a volume for holding venous blood, a blood outlet, and a vacuum port;
    an air sensor for sensing the presence of air within an interior portion of the container near the vacuum port; and
    a vacuum source for automatically supplying vacuum to the vacuum port in response to the air sensor sensing the presence of air.

2. The device as recited in claim 1, and further comprising a filter element disposed within the container.

3. The device as recited in claim 2, wherein the filter element is capable of trapping air bubbles.

4. The device as recited in claim 2, wherein the filter element is disposed between the blood inlet and the blood outlet, such that blood entering the blood inlet is required to pass through the filter element before reaching the blood outlet.

5. The device as recited in claim 2, wherein the filter element has an open central portion in communication with the blood outlet.

6. The device as recited in claim 1, wherein the blood inlet and the blood outlet are arranged on the container such that there is no air space between the blood inlet and the blood outlet during operation of the device.

7. The device as recited in claim 2, wherein the blood inlet and the blood outlet are arranged on the container such that there is no air space between the blood inlet and the blood outlet during operation of the device.

8. The device as recited in claim 1, wherein the blood outlet is disposed on a bottom portion of the container.

9. The device as recited in claim 2, wherein the blood outlet is disposed on a bottom portion of the container.

10. The device as recited in claim 1, wherein the blood inlet is disposed on a top portion of the container.

11. The device as recited in claim 2, wherein the blood inlet is disposed on a top portion of the container.

12. The device as recited in claim 1, and further comprising a blood pump connected to the blood outlet.

13. The device as recited in claim 1, wherein the air sensor senses air in a top portion of the container.

14. The device as recited in claim 13, wherein the top portion of the container includes a convex portion.

15. The device as recited in claim 14, wherein the convex portion of the container is above the filter element.

16. A method for removing air from venous blood of a patient, comprising:
    introducing venous blood through a blood inlet into a container;
    sensing the presence of air within an interior portion of the container with an air sensor;
    automatically withdrawing air from the container by a vacuum source in response to sensing the presence of air until air is no longer sensed within the interior portion of the container; and
    withdrawing blood through a blood outlet.

17. The method as recited in claim 16, and further comprising filtering the blood within the container.

18. The method as recited in claim 17, and further comprising trapping air bubbles as the blood is filtered.

19. The method as recited in claim 18, wherein the trapped air bubbles rise toward a top portion of the container.

20. The method as recited in claim 18, wherein the trapped air bubbles accumulate in a top portion of the container.

21. The method as recited in claim 18, wherein the presence of air is sensed at a top portion of the container.

22. The method as recited in claim 16, and further comprising drawing the blood through a filter as it flows between the blood inlet and the blood outlet.

23. The method as recited in claim 16, and further comprising pumping the blood from the blood outlet.

24. The method as recited in claim 23, wherein the vacuum from the vacuum source is greater than a vacuum created by pumping the blood from the blood outlet.

25. The method as recited in claim 16, wherein the air is withdrawn from the container by the vacuum source when, and only when, the presence of air is sensed by the air sensor in order to prevent blood from being aspirated by the vacuum source.

26. The method as recited in claim 16, and further comprising filling the container with blood.

* * * * *